(12) United States Patent
Le Van Quyen et al.

(10) Patent No.: US 11,612,743 B2
(45) Date of Patent: *Mar. 28, 2023

(54) METHOD AND DEVICE FOR ENHANCING MEMORY CONSOLIDATION

(71) Applicants: ICM (INSTITUT DU CERVEAU ET DE LA MOELLE ÉPINIÈRE), Paris (FR); APHP (ASSISTANCE PUBLIQUE-HÔPITAUX DE PARIS), Paris (FR); CENTRE NATIONAL DE LA RECHERCHE SCIENTIFIQUE (CNRS), Paris (FR); SORBONNE UNIVERSITE, Paris (FR); INSERM (INSTITUT NATIONAL DE LA SANTÉ ET DE LA RECHERCHE MÉDICALE), Paris (FR)

(72) Inventors: Michel Le Van Quyen, Paris (FR); Stéphane Charpier, Paris (FR); Séverine Mahon, Paris (FR)

(73) Assignees: ICM (INSTITUT DU CERVEAU ET DE LA MOELLE ÉPINIÈRE, Paris (FR); APHP (ASSISTANCE PUBLIQUE - HÔPITAUX DE PARIS), Paris (FR); CENTRE NATIONAL DE LA RECHERCHE SCIENTIFIQUE (CNRS), Paris (FR); INSERM (INSTITUT NATIONAL DE LA SANTÉ ET DE LA ECHERCHE MEDICALE), Paris (FR); SORBONNE UNIVERSITE, Paris (FR)

( * ) Notice: Subject to any disclaimer, the term of this patent is extended or adjusted under 35 U.S.C. 154(b) by 576 days.

This patent is subject to a terminal disclaimer.

(21) Appl. No.: 16/751,997

(22) Filed: Jan. 24, 2020

(65) Prior Publication Data
US 2020/0269045 A1  Aug. 27, 2020

Related U.S. Application Data

(63) Continuation of application No. 15/539,092, filed as application No. PCT/EP2015/081050 on Dec. 22, 2015, now Pat. No. 10,561,840.

(30) Foreign Application Priority Data

Dec. 22, 2014  (EP) .................................. 14199909

(51) Int. Cl.
*A61N 1/36* (2006.01)
*A61B 5/00* (2006.01)
(Continued)

(52) U.S. Cl.
CPC .......... *A61N 1/36025* (2013.01); *A61B 5/369* (2021.01); *A61B 5/4812* (2013.01);
(Continued)

(58) Field of Classification Search
CPC ........ A61M 2230/005; A61M 2230/10; A61M 2230/14; A61M 2230/18; A61M 21/02;
(Continued)

(56) References Cited

U.S. PATENT DOCUMENTS

| 8,792,975 B2 | 7/2014 | Kato et al. |
| 10,561,840 B2 | 2/2020 | Le Van Quyen et al. |

(Continued)

FOREIGN PATENT DOCUMENTS

| EP | 2524649 A2 | 11/2012 |
| WO | WO 2011/135789 A1 | 11/2011 |

(Continued)

OTHER PUBLICATIONS

Steriade et al., "Thalamocortical oscillations in the sleeping and aroused brain," Science, vol. 262, Oct. 29, 1993; pp. 679-685.
(Continued)

*Primary Examiner* — Christine H Matthews
*Assistant Examiner* — Joshua Daryl D Lannu
(74) *Attorney, Agent, or Firm* — Osha Bergman Watanabe & Burton LLP

(57) ABSTRACT

The present invention relates to methods and devices to consolidate memory and/or cognitive functions by monitoring brain rhythms and delivering a stimulus at an appropriate stage of sleep cycle.

21 Claims, 9 Drawing Sheets

(51) Int. Cl.
  *A61N 1/04* (2006.01)
  *A61M 21/02* (2006.01)
  *A61B 5/369* (2021.01)

(52) U.S. Cl.
  CPC ........... *A61B 5/6803* (2013.01); *A61M 21/02* (2013.01); *A61N 1/0408* (2013.01); *A61B 5/4088* (2013.01); *A61M 2230/005* (2013.01); *A61M 2230/10* (2013.01); *A61M 2230/14* (2013.01); *A61M 2230/18* (2013.01); *A61M 2230/60* (2013.01)

(58) Field of Classification Search
  CPC .. A61M 2230/60; A61B 5/369; A61B 5/4812; A61B 5/4088; A61B 5/6803; A61N 1/0408; A61N 1/36025
  See application file for complete search history.

(56) References Cited

U.S. PATENT DOCUMENTS

| | | | |
|---|---|---|---|
| 2012/0016431 A1 | 1/2012 | Paul et al. | |
| 2013/0190556 A1* | 7/2013 | Wetmore | A61M 21/00 600/27 |
| 2014/0057232 A1 | 2/2014 | Wetmore et al. | |
| 2017/0361060 A1* | 12/2017 | Garcia Molina | A61M 21/02 |
| 2017/0368348 A1 | 12/2017 | Le Van Quyen et al. | |

FOREIGN PATENT DOCUMENTS

| | | |
|---|---|---|
| WO | WO 2012/138761 A1 | 10/2012 |
| WO | WO 2014/028372 A1 | 2/2014 |

OTHER PUBLICATIONS

Tononi et al., "Sleep function and synaptic homeostasis," Sleep Medicine Reviews, vol. 10 (2006); pp. 49-62.
Destexhe et al., "Are corticothalamic 'up' states fragments of wakefulness?", Trends Neurosci. 30(7), Jul. 2007; pp. 334-342.
Petersen et al., "The functional organization of the barrel cortex," Neuron 56(2), Oct. 25, 2007; pp. 339-355.
Cirelli et al., "Is sleep essential?", PLoS Biology, vol. 6, Issue 8, e216, Aug. 2008; pp. 1605-1611.
Tononi et al., "Enhancing sleep slow waves with natural stimuli," Medicamundi, vol. 54 (2010); pp. 73-79.
Wang et al., "Synaptic plasticity in sleep: learning, homeostasis and disease," Trends Neurosci. 34(9), Sep. 2011; pp. 452-463.
Chauvette et al., "Properties of slow oscillation during slow-wave sleep and anesthesia in cats," J Neurosci. 31(42), Oct. 19, 2011; pp. 14998-15008.
Lu et al., "Does abnormal non-rapid eye movement sleep impair declarative memory consolidation? Disturbed thalamic functions in sleep and memory processing," Sleep Medicine Reviews 16 (2012); pp. 389-394.
Mahon et al., "Bidirectional plasticity of intrinsic excitability controls sensory inputs efficiency in layer 5 barrel cortex neurons in vivo," Journal of Neuroscience 32(33), Aug. 15, 2012; pp. 11377-11389.
Chauvette et al., "Sleep oscillations in the thalamocortical system induce long-term neuronal plasticity," Neuron. 75(6), Sep. 20, 2012; pp. 1105-1113.
Steiger et al., "Pathology of sleep, hormones and depression," Pharmacopsychiatry 46, Suppl.1 (2013); pp. S30-S35.
Germain, A., "Sleep disturbances as the hallmark of PTSD: where are we now?", Am.J.Psychiatry 170(4), Apr. 1, 2013; pp. 372-382.
Ngo et al., "Auditory closed-loop stimulation of the sleep slow oscillation enhances memory," Neuron, vol. 78, May 8, 2013; pp. 545-553.
Daoudal et al., "Long-term plasticity of intrinsic excitability: learning rules and mechanisms," Learning & Memory 10 (2003); pp. 456-465.

* cited by examiner

METHOD AND DEVICE FOR ENHANCING MEMORY CONSOLIDATION

FIELD OF INVENTION

The present invention relates to methods and devices to consolidate memory and/or cognitive functions by monitoring brain rhythms and delivering a stimulus at an appropriate stage of sleep cycle.

BACKGROUND OF INVENTION

Strategies to alleviate or mitigate cognitive deficits with pharmaceutical, educational, and behavioral interventions have received significant attention recently. New methods for improving the lives of those with intellectual disabilities, age-related cognitive decline, and other forms of learning disability by reinforcing and/or consolidating memory and cognitive function are desired. Moreover, healthy, typically-developed students of all ages would benefit from a method for enhancing memory consolidation and thus long-term memory retention.

Sleep has many inherent benefits, including an important role in memory consolidation. Brain rhythms regulate information processing in different states to enable learning and memory formation.

The sleep begins with light sleep (stage I and stage II) which leads quickly to slow-wave sleep (SWS) state (stages 3 and 4). After about 90 minutes, rapid eye movement (REM) sleep appears. These stages are the first sleep cycle. A cycle lasts about 90 minutes. One night has 4 to 6 cycles, depending on the duration of sleep. The first half of sleep is particularly rich in deep sleep, while the second half is essentially constituted by alternating light sleep and REM sleep.

SWS is thought to be critical for many of sleep's restorative effects (Cirelli C, Tononi G 2008 PLoS Biol 6(8): e216). In particular, many convergent experimental findings suggest that sleep slow oscillations (SO, <1 Hz) in the electroencephalogram (EEG), characterized by global up-states (neuronal firing) and down-states (neuronal silence), can promote synaptic downscaling and plasticity and, consequently, may play an active role in learning and memory consolidation (Steriade M, et al 1993 Science 262(5134): 679-85; Tononi, G and Cirelli, C 2006 Sleep Med. Rev. 10, 49-62). In this context, stimuli, in addition to induce evoked-potentials, can affect EEG activity by boosting various sleep brain rhythms and, thus, could provide a tool to artificially improve SO generation (Tononi, G., et al 2010 Medicamundi 54, 73-79). Nevertheless, previous studies imposed simulations on the brain disregarding the phase of ongoing endogenous oscillating activity, which might explain the overall limited enhancement in SO induction (patent applications: WO2012/138761, WO2014/028372).

In addition, a precedent study already tried to stimulate in phase with SO but no increase in SO events was observed nor differences in sleep architecture (Ngo H V, et al. 2013 Neuron 78, 545-553).

Surprisingly, the new method disclosed herein is able to initiate and enhance SO by presenting stimuli (tones, lights, tactile stimulation on the body surface) in synchrony with the brain's own rhythm. More surprisingly the sleep architecture of the subject is modified.

SUMMARY

One object of the present invention relates to a non-invasive method for enhancing and/or consolidating memory in a subject in need thereof comprising:

a. monitoring a subject's sleeping cycle,
b. detecting the end of stage I of a non-REM light sleep state,
c. applying a first stimulus on said subject at the onset of stage II of a non-REM light sleep state,
d. applying a second stimulus on said subject,
e. repeating applying the first stimulus and the second stimulus until the end of stage IV, and
f. restarting said method at step c when an onset of a further stage II is detected, thereby extending slow wave sleep stages and modulating the sleep architecture of said subject.

Another object of the present invention relates to a non-invasive method for enhancing and/or consolidating memory comprising:

a. monitoring sleeping cycle,
b. detecting the end of stage I of a non-REM light sleep state,
c. emitting a first stimulus at the onset of stage II of a non-REM light sleep state,
d. emitting a second stimulus,
e. repeating applying the first stimulus and the second stimulus until the end of stage IV, and
f. restarting said method at step c. when an onset of a further stage II is detected, thereby extending slow wave sleep stages and modulating the sleep architecture.

The present application also relates to a non-invasive method for modulating sleep architecture comprising:

a. monitoring sleeping cycle,
b. detecting the end of stage I of a non-REM light sleep state,
c. emitting a first stimulus at the onset of stage II of a non-REM light sleep state,
d. emitting a second stimulus,
e. repeating applying the first stimulus and the second stimulus until the end of stage IV, and
f. restarting said method at step c. when an onset of a further stage II is detected, thereby improving memory consolidation and/or cognition and/or general well-being.

In one embodiment, said stimulus is a sensory, electrical and/or magnetic stimulus.

In another embodiment, both stimuli are separated for a time comprised from about 1 second to 2 seconds.

In another embodiment, the first stimulus is applied from about 0.1 to about 1 second after the detection of the negative peak.

In another embodiment, the method of the invention further comprises the application of same stimuli during memory training or learning process while said subject is awake.

In another embodiment, the method of the invention is controlled by said subject.

In another embodiment, the method of the invention is controlled by a skilled pratician.

In another embodiment, said subject is a healthy subject which undergoes normal aging or a training period.

In another embodiment, said subject is affected by a memory-related disorder or a cognitive-related disorder.

In another embodiment, said subject is affected by a neuronal connectivity disorder.

Another object of the present invention relates to a device for implementing the method of the invention comprising:

a. a headband to monitor brain activity comprising at least two electrodes, wherein one electrode is an active electrode to detect SOs and the other is the reference electrode placed on the mastoid part of the temporal lobe, b. a stimulation device providing at least one type of stimulus, c. a programmable microcontroller board.

Another object of the present invention relates to a device for implementing the method of the invention comprising:

a. a headband to monitor brain activity comprising at least two electrodes, wherein one electrode is an active electrode to detect the end of stage I of a non-REM light sleep state and the other is the reference electrode placed on the mastoid part of the temporal lobe, b. a stimulation device providing a first stimulus at the onset of stage II of a non-REM light sleep state and a second stimulus separated for a time from about 1 to about 2 seconds, c. a programmable microcontroller board repeating step b. until the end of stage IV, and.

d. said programmable microcontroller board restarting at step a. when an onset of a further stage II is detected.

Definitions

In the present invention, the following terms have the following meanings:

"Affected" refers to the affliction of a subject having and/or developing and/or at risk to develop a sleep-related disorder, memory or a cognitive-related disorder.

"Sleeping state" refers to a progression of brainwave patterns that may be monitored while a subject is sleeping. Generally, subjects undergo several sleep cycles per night, each lasting around ninety minutes. Each progression of brainwave patterns during the sleep cycle may be referred to as a stage of the sleep cycle.

"Sleep cycle" refers to consecutive stages that comprise: a falling asleep state, a non-REM sleep state (light state and then deep state) and briefly back to stage II sleep then REM sleep state (during this stage the brain activity is intense, quite close to that of awakening, there are very rapid eye movements).

"Non-REM sleep state" refers to stage I (stage of transition between wakefulness and sleep), stage II (stage of sleep confirmed), stage III, stage IV sleep (stages III and IV are characterized on the EEG by slow and loose waves, hence the name of slow wave sleep).

"Non-invasive" means that no tissue is taken from the body of a subject.

"About" preceding a figure and/or a score means plus or less 10% of the value of said figure and/or score.

DETAILED DESCRIPTION

This invention relates to a non-invasive method for improving and/or consolidating memory in a subject in need thereof and comprising:

a. monitoring a subject's sleeping cycle, b. detecting the end of stage I of a non-REM light sleep state, c. applying a first stimulus on said subject at the onset of stage II of a non-REM light sleep state, d. applying a second stimulus on said subject, e. repeating applying the first stimulus and the second stimulus until the end of stage IV, and f. restarting said method at step c when an onset of a further stage II is detected, thereby extending slow wave sleep stages and modulating the sleep architecture of said subject.

Technics to monitor sleeping cycle in a subject include but are not limited to: electroencephalography (EEG); electrooculography (EOG); electromyography (EMG); motion during sleep (called actigraphy measured by image capture, accelerometer, microphone, or other techniques); heart rate, via accelerometer, pulse oximetry, ECG; respiratory rate, via accelerometer, microphone; and body temperature, via temperature probe or distant infrared (IR) sensor.

EEG records the neural activity of electrical potential across cell membranes, which are detected through the cerebral cortex and recorded by a plurality of electrodes. The changes in electrical potential in the cortex contain rhythmical activity, which typically occur at frequencies of about 0.5 to 70 cycles per second (hertz). While awake, fast, random signals are predominantly generated at low amplitude voltage and mixed frequency. While asleep, more predictable signals are generated at a high amplitude voltage and predictable frequencies over predictable periods.

Electrooculography (EOG) records the ocular activity of the electrical potential from the retina, which consists of an electrically-charged nerve membrane. EOG signals can be measured by placing electrodes near an eye. Motion of an eye may cause a measurable change of electrical potential between two or more surface electrodes.

Electromyography (EMG) records the muscular activity of electrical potential across muscular membranes, which range between about 50 microvolts to about 300 millivolts (depending on the muscle under observation). Typical repetition rate of muscle unit firing is about 7 hertz to about 200 hertz, depending on the size of the muscle, the type of muscle, etc. EMG signals may be recorded within a muscle (i.e., intramuscular EMG) or on the surface a subject's skin outside of a muscle.

In one embodiment, one or more of those technics may be used simultaneously to monitor sleep cycle.

For example, a subject's EOG and/or EMG may also be useful in determining the sleep cycle of a subject. For example, when phasic burst of EOG eye movements are seen during low EMG activity along with simultaneous low voltage, mixed frequency EEG activity, the subject is likely to be in REM sleep.

Five distinct brain wave patterns that are commonly detected during an EEG recording are delta waves (e.g., about 0.5-3 hertz), theta waves (e.g., about 3-8 hertz), alpha waves (e.g., about 8-12 hertz), beta waves (e.g., about 13-38 hertz), and gamma waves (e.g., about 38-70 hertz). Many of these frequencies may be observed in a subject's sleep cycle. A sleep cycle may be defined as a progression of brainwave patterns that may be seen while a subject is sleeping. Generally, subjects undergo several sleep cycles per night, each lasting around ninety minutes. Each progression of brainwave patterns during the sleep cycle may be referred to as a stage of the sleep cycle. Generally, each sleep cycle progresses consecutively through stage I sleep, stage II sleep, stage III sleep, stage IV sleep (stage III sleep and stage IV sleep may be grouped together and referred to as slow wave sleep), briefly back to stage II sleep, and then REM sleep.

In one embodiment, the stimulus of the invention provided may comprise an electrical or sensory stimulus. One or more forms of sensory stimulation includes, but is not limited to auditory, olfactory, tactile, somatosensory, gustatory, visual, vestibular or other sensory systems stimuli. One or more forms of electrical stimulation include, but is not limited to: transcranial electrical stimulation. Other forms of stimuli include but are limited to: ultrasound, optical, magnetic, transcranial magnetic stimulation or another form of energy. Accordingly, the skilled artisan knows the best way of applying each of these stimuli.

In another embodiment, the stimulus of the invention comprises bone stimulation. In particular, the bone stimulation includes the vibration of the bones of the inner ear.

In another embodiment, the stimulus of the invention is osteophonic stimulation.

In one embodiment, the choice of the stimuli is adapted to each subject depending on its sensitivity and/or ability to receive said stimuli.

In another embodiment, the intensity of the stimuli is adapted to each subject depending on its sensitivity and/or ability to receive said stimuli.

In a further aspect of the invention, the stimulus described here above is applied while the subject is awake and is undergoing a training period or a learning process.

In another embodiment, a sensory stimulator is configured to provide an ambient sensory stimulus recorded during the training session. For example, the sensory stimulator may comprise an ambient recorder for recording the ambient stimulus wherein the ambient recorder is configured to record one or more of ambient sounds, ambient odors, and ambient sensations.

In another embodiment, the stimulus may be optimized. In some variations, the sensory stimulus provided may be optimized based on the information to be learned. For example, the stimulus provided may be non-interruptive, and may be configured to be innocuous so as not to interrupt the concentration of the user during the training session and/or not to awaken or disrupt the user's sleep during sleep consolidation.

In another embodiment, the stimulus is provided by third parties (e.g. advertisers) who pay to have a user train with a particular scent, jingle, or other stimulus during training with the device. In another embodiment, a user could purchase a single stimulus or set of stimuli similar to how one buys a ringtone or rights to a copyright-controlled stock image.

In one embodiment, the stimulus is unique to a particular learning session or subject matter. Thus, in variations the linking of the sensory stimulus to the subject matter may allow association across training sessions. For example, in some variations the system (e.g., using control or system logic) may select stimuli for the purpose of invoking transitive inference between content to be learned. In a simple example, a user desires to associate the word "orange" with the picture of an orange. While being presented with an olfactory cue, the user is also presented the word "orange." In another learning event, the same olfactory cue is co-presented with the picture of an orange. The user subsequently uses transitive inference to associate the word with the picture, without having a simultaneous presentation of the two items.

In another embodiment, the stimulator is a non-distracting stimulus.

In another embodiment, the stimulator cannot awake the subject of the invention.

In one embodiment, the subject may configure the stimulation to deliver different types of stimulation to, e.g., correspond to different types of awake learning tasks.

For example, a subject may configure an auditory stimulation device to deliver a first type of auditory or olfactory stimulation, such as, e.g., classical music (or classical music of a specific composer), while the subject is learning a selected type of material (e.g., math, grammar, history, etc.).

In another example, a subject may configure the auditory stimulation device to deliver a second type of auditory stimulation, such as, e.g., ambient "water flowing" sounds, while the subject is learning vocabulary. Still further, for example, a subject may configure the auditory stimulation device to deliver a third type of auditory stimulation, such as, e.g., short auditory tones (e.g., about 1 kilohertz or more, 2 kilohertz or less, etc. for about one-half second or less, about 1 second or more, about 1 second or less, etc.), that are selected to correspond to a selected learning activity.

In another embodiment, the stimulation is applied after detection of the end of stage I of a non-REM-sleep state.

In another embodiment, the stimulation is applied after detection of the onset of stage II of a non-REM-sleep state.

In one embodiment, the stimulation is applied after detection of a specific phase of ongoing SO. In one embodiment, the stimulation is applied at the detection of negative peaks of SO.

In one embodiment, the first stimulation is applied at the detection of negative peaks of SO and the second stimulation is applied at the detection of positive peak of SO.

SOs rhythms are different from a subject to another. Therefore, the method of the invention can adapt the stimulation to each subject.

In one embodiment, the stimulation applied in the method of the invention enhances other rhythms than slow waves.

In one embodiment, the stimulation is applied at the detection of sleep spindles. Sleep spindles are bursts of brain waves that may be networking between key regions of the brain to clear a path to learning. These electrical impulses help to shift fact-based memories from the brain's hippocampus, which has limited storage space, to the prefrontal cortex's "hard drive", thus freeing up the hippocampus to take in fresh data. Spindles are fast pulses of electricity generated during non-REM sleep, and they can occur up to 1,000 times a night. This spindle-driven networking is most likely to happen during stage II of non-REM sleep, which occurs before we reach the deepest non-REM sleep and the dream state known as REM sleep.

In another embodiment, the stimulation is applied when a peak is having amplitude inferior to −75 µV. In another embodiment, the stimulation is applied when a peak is having an amplitude from about 50 to about 150 µV.

Methods to detect negative peaks are well known in the state of the art and are described hereabove.

In one embodiment, the non-invasive method of the invention comprises the application of stimuli that are separated for a time comprised from about 1 second to about 2 seconds. In another embodiment, the time comprised between stimuli applications is adapted to each subject.

In one embodiment, the non-invasive method of the invention comprises the application of first stimuli that are separated for a time comprised from about 0.1 to about 1 second, preferably 0.4 to 0.6 seconds after the detection of the negative peak. Most preferably, the non-invasive method of the invention comprises the application of first stimuli that are separated for a time of about 0.5 seconds after the detection of the negative peak. After the first intervention (stimuli), a second stimulus is triggered with a delay of about 0.8; 0.9; 1; 1.1; 1.2; 1.3; 1.4; 1.5; 1.6; 1.7; 1.8; 1.9 seconds. Preferably, the non-invasive method of the invention comprises the application of a second stimulus separated for a time of about 1.25 seconds from the first stimulus. In another embodiment, the non-invasive method of the intervention comprises the application of train of several stimuli that are separated for a time of about 1.25 seconds after the first intervention.

The person skilled in the art knows that sleep cycle is different from a subject to another depending on diverse factors that include but are not limited to: age, sex, environmental conditions, a disease that might affect said subject etc. . . . .

In one embodiment, said intensity of said first and second stimuli is equal.

In another embodiment, said intensity of said first stimulus is lower than the intensity of the second stimulus.

In another embodiment, said intensity of said first stimulus is higher than the intensity of the second stimulus.

In one embodiment, the length of an auditory stimulation is from about 25 to about 100 ms, preferably 50 ms.

In another embodiment, the length of an auditory stimulation is 50 ms.

In another embodiment, the length of an auditory stimulation is adapted to each subject.

In one embodiment, the amplitude of an auditory stimulus is from 40 to 70 dB.

In another embodiment, the amplitude of an auditory stimulus is about 65 dB.

In another embodiment, the amplitude of an auditory stimulation is adapted to each subject.

In one embodiment, the intensity of transcranial electrical stimulations is from about 0.3 to about 0.2 mA.

In another embodiment, the frequency of transcranial electrical stimulations is from about 0.5 to about 1 Hz, preferably about 0.8 Hz.

In one embodiment, said non-invasive method is performed at the hospital.

In another embodiment, said non-invasive method is performed at home.

In one embodiment, said non-invasive method is controlled by the subject.

In another embodiment, said non-invasive method is controlled by the skilled pratician.

In one embodiment, the subject of the invention is a mammal, preferably a human. In one embodiment, the subject is female. In another embodiment the subject is a male.

In one embodiment, the subject of the invention is an adult. In one embodiment, the term "adult" may refer to subjects of more than 20 years old to about 65 years old.

In another embodiment, the subject of the invention is a young subject. In one embodiment, the term "young subject" may refer to subjects from about 8 to about 20 years old.

In another embodiment, the subject of the invention is a senior person. The term "senior person" may refer to subjects from about 65 years old.

In another embodiment, the subject is a healthy subject which undergoes normal aging.

In another embodiment, the subject is a healthy subject which undergoes a training period.

In another embodiment, the subject of the invention is affected by a sleep-related disorder.

In another embodiment, the subject of the invention is not affected by a sleep-related disorder.

In another embodiment, the subject of the invention is affected by epilepsy.

In one embodiment, the subject of the invention is not affected by a depressive disorder.

In another embodiment, the subject of the invention is affected by a memory-related disorder or a cognitive-related disorder. Examples of memory or cognitive-related disorders include but are not limited to: Alzheimer's disease, Down syndrome, Parkinson's disease, frontotemporal dementia, epilepsy, stroke, Rett syndrome, Huntington's disease, autism spectrum disorder, Fragile X syndrome, neurofibromatosis type 1, tuberous sclerosis, phenylketonuria, maple syrup urine disease, chemotherapy treatment, radiation therapy, post-traumatic stress disorder, drug or alcohol use.

In another embodiment, the subject of the invention is affected by a neuronal connectivity disorder in the absence of obvious anatomical, proliferative or degenerative anomaly. Examples of such disorders include in a non-limited list: schizophrenia and other psychiatric disorders, and autism.

This invention also relates to a non-invasive method for enhancing and/or consolidating memory comprising:
  a. monitoring sleeping cycle,
  b. detecting the end of stage I of a non-REM light sleep state,
  c. emitting a first stimulus at the onset of stage II of a non-REM light sleep state,
  d. emitting a second stimulus,
  e. repeating applying the first stimulus and the second stimulus until the end of stage IV, and
  f. restarting said method at step c. when an onset of a further stage II is detected, thereby extending slow wave sleep stages and modulating the sleep architecture.

The present application also relates to a non-invasive method for modulating sleep architecture comprising:
  a. monitoring sleeping cycle,
  b. detecting the end of stage I of a non-REM light sleep state,
  c. emitting a first stimulus at the onset of stage II of a non-REM light sleep state,
  d. emitting a second stimulus,
  e. repeating applying the first stimulus and the second stimulus until the end of stage IV, and
  f. restarting said method at step c. when an onset of a further stage II is detected,
thereby improving memory consolidation and/or cognition and/or general well-being.

The term "modulating sleep architecture" as used herein refers to an extension or a reduction of slow wave sleep stages. The technics to determine a modulation of sleep architecture are well known to the skilled artisan and are described here above.

In one embodiment, the method of the invention aims at improving the sleep quality and efficiency in a subject, as measured and scored quantitatively during sleep, upon awakening, and during waking hours, for short, medium, and long periods of time.

The present application also relates to a device for implementing the methods of the present application to a subject in need thereof.

In one embodiment, the device of the present application comprises:
  a. a headband to monitor brain activity comprising at least two electrodes, wherein one electrode is an active electrode to detect SOs and the other is the reference electrode placed on the mastoid part of the temporal lobe,
  b. a stimulation device providing at least one type of stimulus,
  c. a programmable microcontroller board.

The present application also relates to a device comprising:
  a. a headband to monitor brain activity comprising at least two electrodes, wherein one electrode is an active electrode to detect the end of stage I of a non-REM light sleep state and the other is the reference electrode placed on the mastoid part of the temporal lobe,
b. a stimulation device providing a first stimulus at the onset of stage II of a non-REM light sleep state and a second stimulus separated for a time from about 1 to about 2 seconds,
c. a programmable microcontroller board repeating step b. until the end of stage IV, and.
d. said programmable microcontroller board restarting at step a. when an onset of a further stage II is detected.

The present application also relates to a device comprising:
a. a headband to monitor brain activity comprising at least two electrodes, wherein one electrode is an active electrode to detect the end of stage I of a non-REM light sleep state and the other is the reference electrode placed on the mastoid part of the temporal lobe,
b. a stimulation device providing a first stimulus at the onset of stage II of a non-REM light sleep state from about 0.1 to about 1 second after the detection of the negative peak and a second stimulus separated for a time from about 1 to about 2 seconds,
c. a programmable microcontroller board repeating step b. until the end of stage IV, and.
d. said programmable microcontroller board restarting at step a. when an onset of a further stage II is detected.

In one embodiment, the device may include a power supply, a control system, a display system, at least one electrode, and/or any other component as would be known by the skilled artisan. The monitoring device may be autonomous, or may be operated by an operator.

Electrodes of the invention include but are not limited to: dry electrodes, cloth electrode, gel electrode, disposable electrode, reusable electrodes, integrated gel electrode, needle electrode.

In one embodiment, the subject may self-administer the device. In one embodiment, the device may be stationary or portable (in which case it may include a portable power supply).

The present application also relates to a monitoring device which can determine the brain activity of said subject. The electrodes of the device may be positioned proximate the subject's head to monitor, e.g., one or more selected portions of the subject's brain and/or head, etc. For example, the electrodes may be positioned proximate the subject's eyes, forehead, frontal lobes, temporal lobes, parietal lobes, occipital lobes, the cerebral cortex overlaying the hippocampus, amygdala, etc. In one embodiment, the reference electrode is positioned in the mastoid part of the temporal bone behind the ear. The one or more selected portions of the subject's brain and/or head to be monitored by the device may be selected based on what portions of the brain may be involved in the task at hand. Additionally, the monitoring device may monitor the state of consciousness or sleep stage the subject is in at any given moment. For example, a subject's frontal lobe just above the eye may be monitored by the device because the stage of sleep may be determined through an analysis of brain waves (e.g., EEG), eye movements (e.g., EOG), and muscle tone (e.g., EMG).

In one embodiment, the device of the invention includes a headband to monitor brain activity of said subject. In particular, the headband may comprise electrodes to monitor EEG signals, EOG, EMG, electrode reference. A headband and signal processing unit may be charged by placing the unit on a docking station mounted on the top of the enclosure. The docking station may be connected to an EEG PCB board that includes various signal processing and wireless communication functionalities. Placing the headband unit in the docking station matches the headband unit to the EEG PCB board for subsequent wireless communication. The EEG PCB board in this example also includes a serial communication port that transmits a serial stream of data corresponding to the user's sleep state, time stamps, and other information. The serial stream is received and parsed by the programmable microcontroller.

In one embodiment, the device of the invention further comprises filters, in particular filters adapted to SO patterns. The EEG signal is filtered out so that the raw EEG data can be graphically displayed and the EOG signals can be filtered. The EOG signals may be filtered using the known JADE algorithm to filter noise. Then, the EEG and EOG signals are low pass filtered and then the signals are Hanning windowed. The filtered EEG data signals are generated and can be graphed. Then, the filtered signals are analyzed for their power spectrum, which are then fed into the neuro-algorithms so that the mental and emotional states of the user are determined. Using the power spectrum analysis, the power spectrum data for the delta, theta, alpha and beta waves are extracted. Examples of filters include but are not limited to Chebyshev Type II filters, Butterworth filters and elliptic filters.

In one embodiment, the device of the invention further comprises filtering an EEG signal of a user, comparing two filtered bands of the EEG signal through spectral analysis, and extracting stable phase-difference (e.g., decoupling) or phase-locking (e.g., coupling) episodes between the two signal bands via statistical identification of phase-locking synchrony.

In this embodiment, a programmable microcontroller board applies control logic that determines device function based on user inputs, the user's sleep state or state of wakefulness, and previous device use by the user. For example, an Arduino open source microcontroller framework is an effective programmable microcontroller board used in this embodiment. The Arduino system includes digital inputs and outputs, analog inputs and outputs, serial receiver, serial transmission, and power (both 5V and 3.3V). The microcontroller system in this example is programmed with custom software for controlling the various elements of the system for memory enhancement.

In one embodiment, the microcontroller begins by first checking whether the device is in Training Mode or Sleep Mode. If the device is in Sleep Mode, the microcontroller begins reading information via a serial communications receiver in real-time from sleep-phase detection circuitry. When the user puts on the EEG headband unit, an LED indicator (the headband LED indicator, LED1) is turned on by changing the appropriate digital output of the microcontroller to a high (5V) state. The microcontroller parses sleep stage information for the user and stores these data with timestamps in a memory component of the device. If the incoming sleep data indicates the user is in a slow-wave sleep epoch, scent delivery logic is activated by changing the appropriate digital output to a high (5V) state. The activation of the scent delivery logic is also registered on the memory component of the device with a timestamp. While slow-wave sleep is occurring, the time of operation is identified and compared to a training schedule, such that on appropriate days, scents are delivered. The device loads, reads, and parses a user configuration file stored on the device memory to determine the appropriate device function based on the training schedule for the user. The selection of which scent to deliver and the quantity of scent delivered is also determined by the training schedule. An LED indicator, stimulus indicator (the scent LED indicator, LED2), is turned on when the scent is delivered during sleep by changing the appropriate digital output of the microcontroller to a high (5V) state. The LED indicator can be left on for the remaining portion of the night so that the user can observe it upon wakening. In such embodiments, the control logic turns off LED2 at a fixed time (e.g. 2 hours) after the user wakes. When the slow-wave sleep epoch ends as determined by the registration of a different sleep state by the sleep state monitoring components of the system, the scent delivery logic is changed to inactive and scent release ceases. While the subject is in non-slow wave sleep states, scent delivery logic is not active. If the device is not being used during sleep, the microcontroller does not acquire sleep information from the associated EEG hardware and no scents are released.

If the device is in Training Mode, the microcontroller digital outputs are changed to high (5V) for LED2 and the appropriate scent delivery unit as determined by the training schedule for the user. At the end of a Training Mode session, the user toggles the position of the user interface switch and the microcontroller responds by changing the appropriate digital outputs to turn off LED2 and cease scent delivery.

In one embodiment, the device described herein may combine multiple modules into a cohesive system. These modules or components may include control logic (e.g., software, firmware, hardware, or the like) which matches learning content with associated sensory stimuli delivered, and hardware (e.g., sensory stimulators) such as scent dispensers or audio speakers and/or recorders. During sleep, monitoring hardware such as electroencephalography (EEG) for recording brain rhythms may be analyzed by logic (e.g., algorithms or logic for detecting deep sleep, such as slow-wave, or delta, 0.5-4 Hz, rhythms in the EEG signal) or other sleep stages and then triggering presentation of sensory stimuli (e.g., sounds or smells).

In another embodiment, the device may include sleep monitoring that can identify particular stages of sleep and communicate this information to a device that determines whether to deliver sensory stimuli and, if so, which sensory stimuli to deliver at which sleep stage to a particular user. In one embodiment, sleep monitoring may be accomplished by electroencephalography (EEG) and the sleep state during which sensory stimuli are delivered may be deep sleep identified on the basis of one or more brain rhythms such as delta rhythms (generally about 0.5-4 Hz) and/or the absence of muscle activity related to eye or other movements generally indicative of other stages of sleep.

In another embodiment, the quantity or quality (e.g. intensity) of a particular stage of sleep that may be deep sleep can be increased or decreased by delivering sensory stimuli or electrical stimulation.

In another embodiment, the choice of sensory stimulus and/or its intensity and/or its rate of repetition can be adjusted based on the level of arousal of the user during sleep.

In another embodiment, performance may be monitored by the system to test memory performance the following day. The platform may use wireless and internet-based networking technologies to access a database that may include learning content, sensory stimuli, and/or sleep monitoring parameters in order to optimize system performance for an individual user or patient population.

In a further embodiment, the device comprises a stimulation device. Stimulation device may include, e.g., a power supply, a control system, a display system, headphones, speakers, tapes, compact discs, memory, tactile pad or tablet, scent release system and/or any other component as would be known by the skilled artisan. The monitoring stimulation device may work in conjunction with a portable audio device like, e.g., an Apple iPod, a MP3 player, a compact disc (CD) player, etc. Further, the stimulation device may be a non-portable audio device like, e.g., a home stereo system, radio, etc.

In another embodiment, the device may include one or a plurality of user interface components that allow a user to control whether the device is in training mode. The user interface is generally configured so that the device may be controlled by the user without requiring additional assistance. The user interface may also allow the user to select other parameters of device function. The device may also include one or a plurality of stimulus generators (optionally referred to as stimulus actuators) capable of activating at least one sensory transduction pathway. The device may also include one or a plurality of sensors that measure user physiology to determine the sleep state of the user. The device may include logic that estimates the sleep state of a user from recorded physiological and other data. The device may also include a controller comprising control logic that determines the device function based on user inputs, the user's sleep state or wakefulness, and previous device use cases by the user.

In another embodiment, the device also includes one more outputs (user outputs) such as screens, light emitting diodes (LEDs), or other components to indicate device function. The device may also include one or more switches or other control elements for the user to control device function. In some variations the device includes a computer-readable/writeable memory component (local or remote). In another embodiment, the device includes a controller and control logic; the device may also include send/receive sub-systems for transmission of data between the device and an off-site computer.

In one embodiment, the device includes a secured system for transmission of data to the skilled patrician, or a medical care unit able to analyze such data. In one embodiment, such data may be used for a research program or used for a reference value in cohort study. In another embodiment, such data may be used for medical care.

In another embodiment, a wireless communication system (Bluetooth) may be provided to transmit the raw and/or processed signals to an EEG receiver board component of the device. In particular, EEG signals are analyzed by the skilled patrician to adapt the method of the invention to the subject in need thereof.

In one embodiment, the device may be controlled externally. For instance, the stimuli train is adapted to each subject by the skilled patrician by a controlled feedback system on the device of the invention.

In one embodiment, the device of the invention may use training optimization algorithms to determine what content is presented at what interval to reduce the amount of time required for training.

In another embodiment, the device described herein may also include logic for efficient memory training and memory consolidation during sleep. In some embodiments, an additional aspect of feedback is used to optimize (or improve) the frequency of repetition by recording on the device itself or through the Internet on a remote server, or through an intermediate device. Established techniques for optimizing the repetition time in a spaced repetition implementation may be based on detailed mathematical models of learning and may take into account the opportunity cost of forgetting and content repetition. These algorithms can be used to improve the performance of the present invention for a particular user, subset of users, or class of users defined by age, gender, cognitive ability, interests, or any clinically relevant cause of cognitive dysfunction.

In one embodiment, optimization can be applied to various components of the present application, including the rate of repetition of training stimuli, the amount of learned material or specific set of content associated with a particular stimulus or class of stimuli, the salience of stimuli associated with training stimuli, or other aspects.

In another embodiment, the device may use analytical and/or data mining techniques to determine interests, experiences, and/or previously learned content in order to select a stimulus or set of stimuli that engage transitive inference processes between previous experience and new learning content. These techniques may be provided as logic (e.g., stimulus selection logic) configured as hardware, software, firmware, or the like.

In another embodiment, an automated algorithm (relationship logic) determines which content that has been added to a user's content database is related, similar or coupled (e.g. all the state capitals, the word 'sleeping' in different languages, or a sequence of steps required to perform CPR), then applies the same sensory stimulus (e.g. the sound of snoring or the scent of a rose) for these pieces of training content, even if the learning events are separated in time by minutes, hours, days, weeks, months, or years. This embodiment may be considered as related to the concept of transitive inference. In a related embodiment, a curated service, third party, or socially-derived network may determine whether content to be learned is related, similar or coupled and may use this determination to determine whether the same or similar sensory stimulus should be presented for these items of content to be learned. In another embodiment, the determination of whether training content is related for purposes of choosing identical or similar stimuli to present during training may be made based on whether other users have coupled such content. For instance, if other users had experienced memory improvements due to transitive inference by using a similar stimulus to associate with content to be learned.

In one embodiment, the device of the invention monitors the user to automatically determine the sleep phase for the subject, and trigger replay of the sensory stimulus upon or after detection of a particular sleep phase. The sleep phase may be a typical sleep stage (e.g., slow-wave sleep) or a variation of a typical sleep stage.

In one embodiment, the device described herein may be configured so that the specified sleep stage is predetermined from the known sleep stages (e.g., slow wave sleep, light sleep, REM sleep, phases S1, S2, S3, or S4 of non-REM sleep, etc.) or combinations of sleep stages. For example, in some variations the sleep stage is slow wave sleep. In some variations (e.g., for reconsolidation of amygdala memories that may be important for PTSD) the sleep stage is rapid eye movement sleep.

In another embodiment, the device described herein may comprise the use of one or more techniques (e.g., electrical stimulation, sensory stimulation or other methods) to induce brain rhythms at delta frequencies to modulate the functional properties of slow-wave sleep to improve memory consolidation processes. Similarly, the device of the invention may use electrical stimulation, sensory stimulation or other methods to disrupt brain rhythms at delta frequencies to modulate the functional properties of slow-wave sleep to interfere with memory consolidation processes. Electrical stimulation, sensory stimulation or other techniques may be used to induce brain rhythms at other frequencies or with other spatial temporal patterns in order to affect brain rhythms and underlying cognitive processes.

In another embodiment, the device of the invention described herein use feedback from recording or monitoring of physiological or other parameters that correspond to sleep state or arousal level to define the intensity, modality, and/or specific stimulus delivered during sleep.

In another embodiment, described herein are methods for improving memory. These methods may have a training mode and a sleep consolidation mode, and may include: a user interface comprising a control allowing a user to switch the device to the training mode to indicate a training session; a sensory stimulator configured to provide a plurality of distinct sensory stimuli; a sleep monitor configured to monitor a user's sleep state; and a controller comprising control logic receiving input from the user interface and configured to select a distinct sensory stimulus for a specific training session and to control the application of the distinct stimulus during the specific training session, and further wherein the controller receives information on the user's sleep state from the sleep monitor, and controls the sensory stimulator to apply the distinct sensory stimulus from the specific training session when the user is experiencing a specified sleep stage during a sleep consolidation mode following the specific training session.

In some embodiments, the device described herein may include a memory (e.g., a computer or digitally readable/writable memory). This memory may be connected directly or remotely to the controller. The memory may be configured to store information that indicates one or more of: which sensory stimuli have been applied for specific training sessions, the sleep state of user, and completion of application of a sensory stimulus during a sleep consolidation mode following a specific training session. In some variation the memory is important for storing and providing user configuration. For example, the device may read a user configuration file or memory to determine what sensory stimuli have been used, or are available for use, and/or for determining what training has occurred, or has been paired with a sensory stimuli. The configuration file may also store user information (e.g., biometric information) and/or access information. The controller may be configured to read information from the memory.

In general, the user interface is adapted so that the user may readily and easily control operation of the device. For example, the user interface may include at least one of: a switch, a toggle, a button, a slider, a knob, or a touchscreen, and may indicate (via instructions, menus, or the like) what options the user may select. The user interface may provide visual, audible, or tactile feedback on the status or operation of the device.

In some embodiments, any appropriate sleep monitor may be used. The device may include sleep monitoring logic to determine (based typically on information provided by a sleep monitor) what sleep state the user is in. This determination may be probabilistic (e.g., the logic may indicate a user is in a particular sleep state, or is not even sleeping, when user indicators (e.g., movement indicators, thermal indicators, electrical indicators, etc.) indicate that the likelihood of a particular sleep state is above some threshold). In some variations the sleep monitor comprises a non-contact sleep monitor. For example, the sleep monitor may be positioned near the sleeping user and may indicate (based on motion) an approximation of which sleep state the user is in.

In some embodiments, the device described herein may include a handle. In general, the device of the invention is intended for a user to operate without requiring additional assistance, at home (e.g., for personal use).

In some embodiments, the device described herein may include a communication module coupled to the controller configured to allow communication with a remote site. For example, also described herein are portable user-controllable devices for improving memory, the device comprising: a user interface comprising a control allowing a user to place the device into a training mode indicating a training session; a sensory stimulator configured to present a plurality of distinct sensory stimuli; sleep monitoring logic configured to determine when the user is in a specified sleep state; and a controller comprising control logic configured to determine a specific sensory stimulus received by the user concurrent with a particular training session; wherein the controller is further configured to reapply the specific sensory stimulus when the user is in a specified sleep state following the training session. As mentioned, the portable device may include a housing at least partially enclosing the user interface, sensory stimulator, and controller. The portable device may also include a sleep monitor configured to monitor the user's sleep state.

In one embodiment, the device described herein may be configured to use ambient sensory stimuli, including ambient noise. In some variations the system or device may therefore include an ambient recorder for recording the ambient stimulus. The ambient recorder may be part of the sensory stimulator, or it may be a separate element. For example, an ambient recorder may be configured to record one or more of ambient sounds, ambient odors, and ambient sensations.

In another embodiment, the sensory stimulator is configured to access one or more sources of ambient stimuli that are active during the training session. The one or more sources of ambient stimuli may include one or more of: audio players, computers, televisions, mobile devices, scent releasing devices, and massage/vibratory devices, or any other device configured to deliver a sensory stimulus to the user.

In another embodiment, the device of the invention comprises methods for improving memory with a user-controlled device. For example, the method may include the steps of: selecting, in a user-controlled device, a specific sensory stimulus that is received by the user during a first learning period; detecting, with the user-controlled device, a specified sleep stage in the user following the first learning period; and delivering, from the user-controlled device, the specific sensory stimulus to the user during the specified sleep stage following the first learning period.

In another embodiment, the method of the invention further includes delivering, from the user-controlled device, the specific sensory stimulus to the user during the first learning period. In some variations the method includes using ambient sensory stimuli. For example, the method may include selecting the specific sensory stimulus by recording an ambient sensory stimulus during the first learning period.

In one embodiment, the method and device of the invention are useful for achieving effective modulation of memory consolidation during sleep.

In another embodiment, the method and device of the invention achieve effective modulation of cognition or memory over one or more days and/or nights, including devices and methods for configuring, populating, and querying a learning database with training content and contextual sensory stimuli co-presented with the training content, as well as devices for selecting, prioritizing, and scheduling contextual sensory stimuli to be presented during study and sleep. The device of the invention is configured to determine how to use training content from the learning database to determine a training schedule for repetition of sensory stimuli associated with particular training content over one or multiple nights of sleep.

EXAMPLES

The present invention is further illustrated by the following examples.

Example 1

In Vivo Experiments in Human Brain

Figure 1:
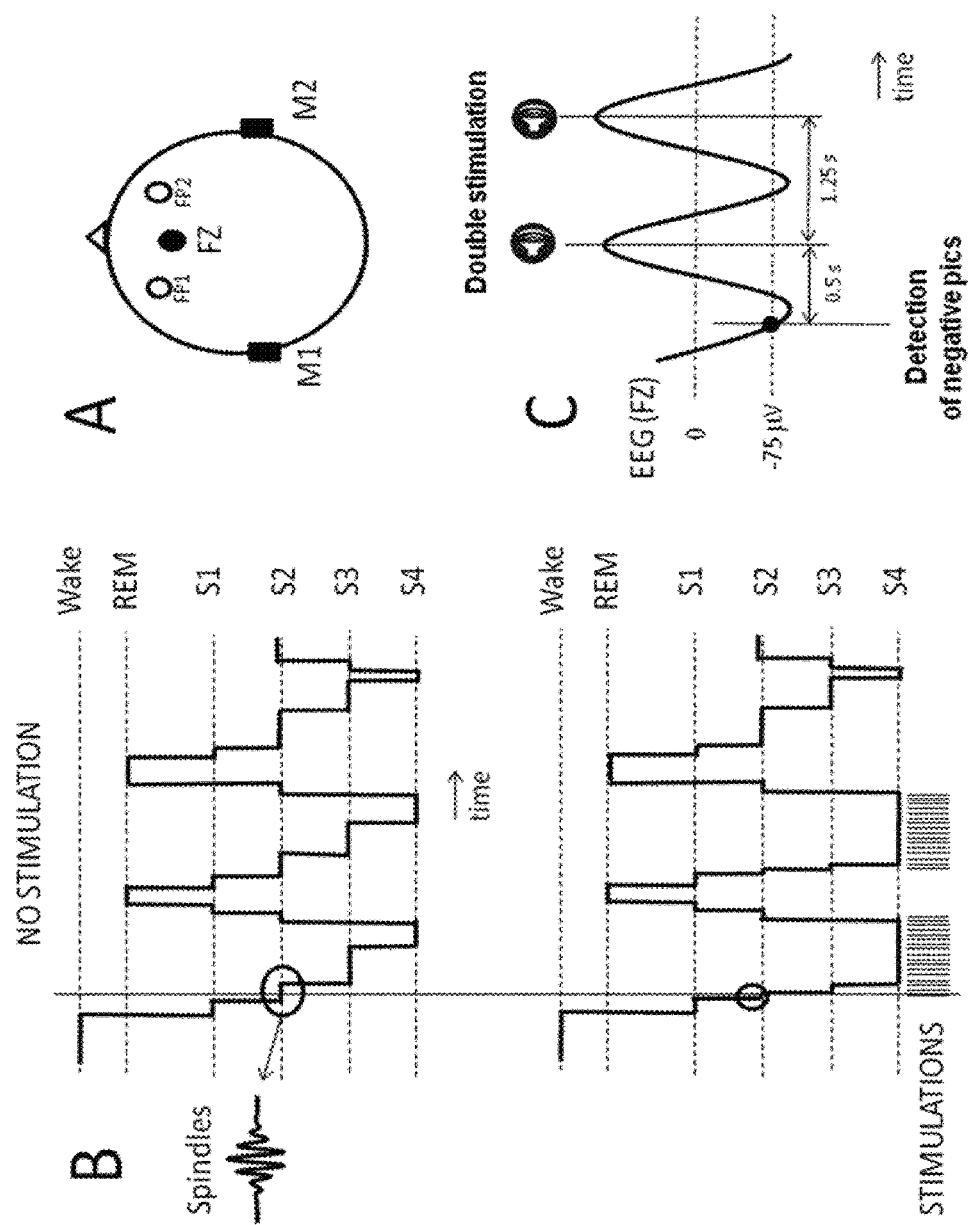
FIG. 1 represents diagrams showing stimulation procedures in human brain.
Figure 2:
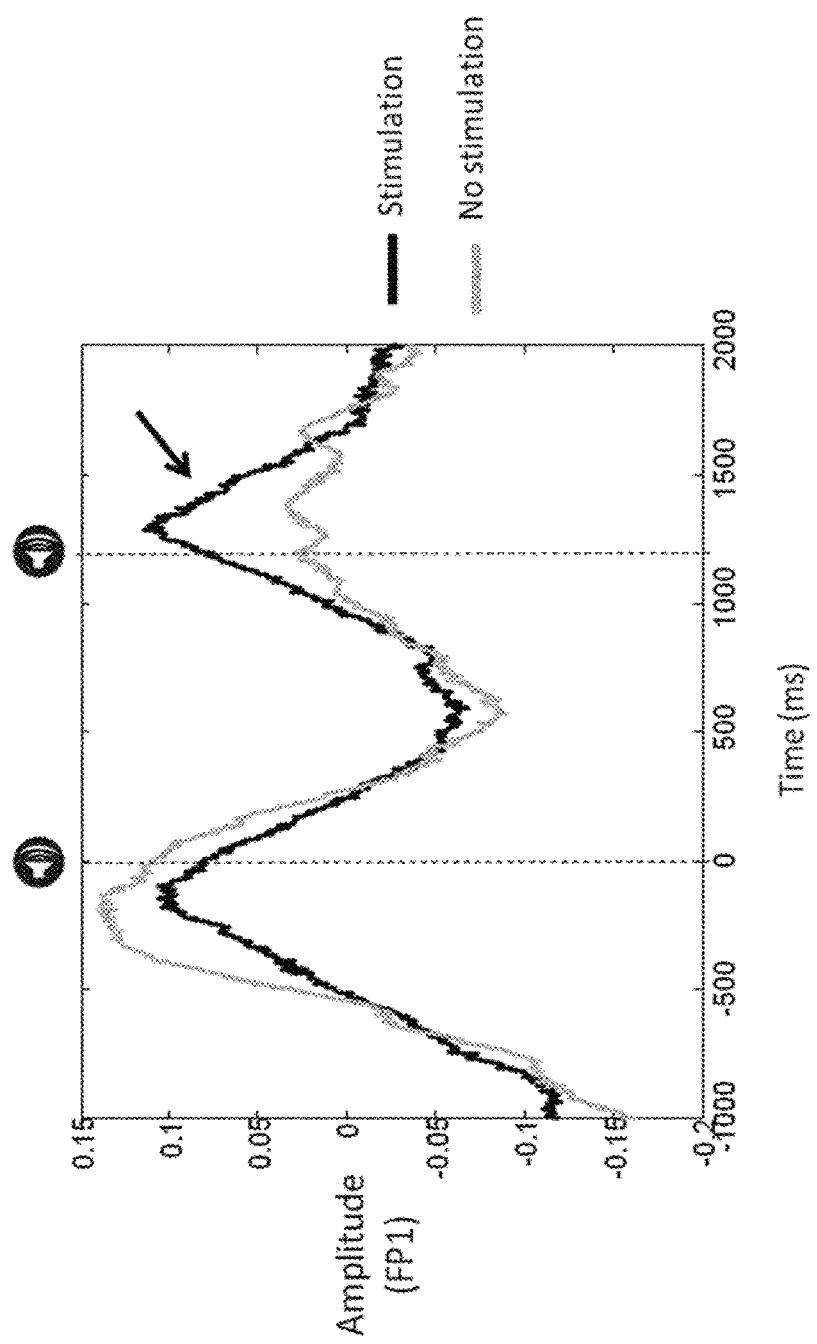
FIG. 2 is a histogram showing the effect of stimulation on the amplitude of sleep slow oscillations.
Figure 3:
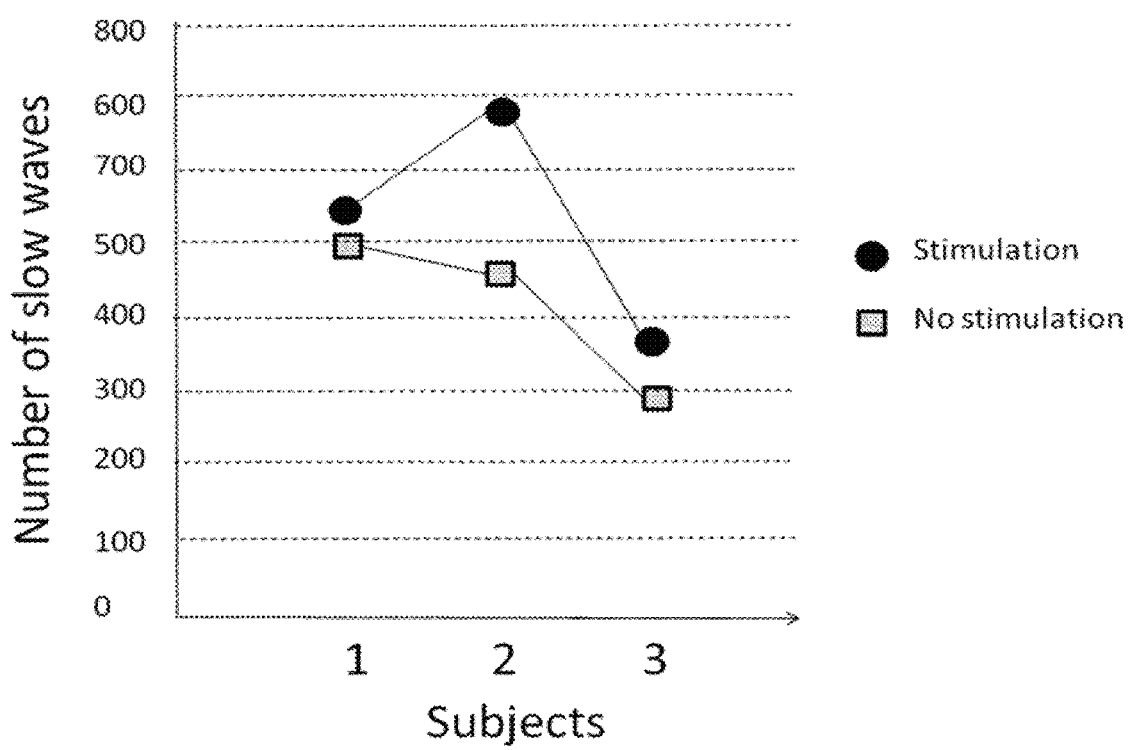
FIG. 3 is a graph showing the effect of stimulation on the number of slow waves sleep.

In human subjects, brain activity is monitored online from a single channel (international 10-20 system, FPZ or Fp1 or Fp2) referenced to the average potential from electrodes attached to the mastoids (M1 and M2) (FIG. 1-A). During sleep, the stimuli are presented for the first time at the onset of stage 2 (associated with sleep spindles at 11 to 15 Hz) (FIG. 1-B). Furthermore, the stimulations are given at a specific phase of ongoing SO. For this purpose, the EEG is recorded and filtered online below 3 Hz using an equiripple Finite Impulse Response (FIR) filters. Each time the filtered EEG signal crossed an adaptive threshold set at large negative values (default −75 μV), two auditory stimulations are triggered (FIG. 1-C). A command sends the sensory stimulation 500 ms after the detection. Then, a second stimulation is provided 1.25 sec after first stimuli. For auditory stimulations, the tones are bursts of pink 1/f noise of 50 ms duration. Sound volume was calibrated to 65 dB SPL. Using this closed-loop feedback system, this system is able to enhance and extend trains of SOs during sleep (FIGS. 2-3).

Figure 4:
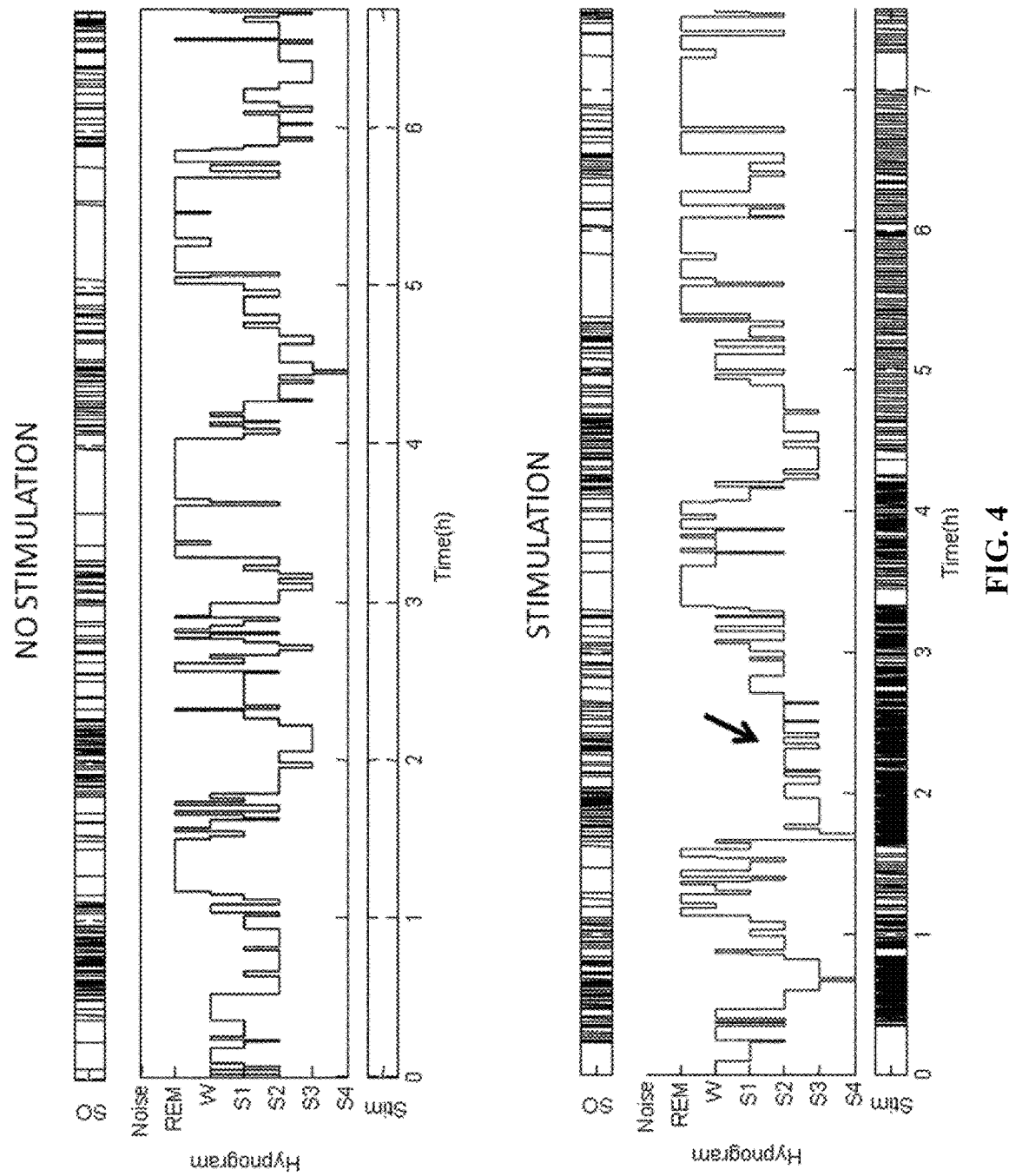
FIG. 4 represents recordings of the sleep architecture before and after stimulation of the human subject.

In contrast to previous reports (Ngo H V, et al. 2013 Neuron 78, 545-553), the increased occurrence of SO trains after stimulation translates into an overall increased number of identified SO in SWS. Furthermore, the system induces significant differences in sleep architecture during the stimulation period and extends SWS stages (FIG. 4).

Example 2

In Vivo Experiments in Animals

Figure 5:
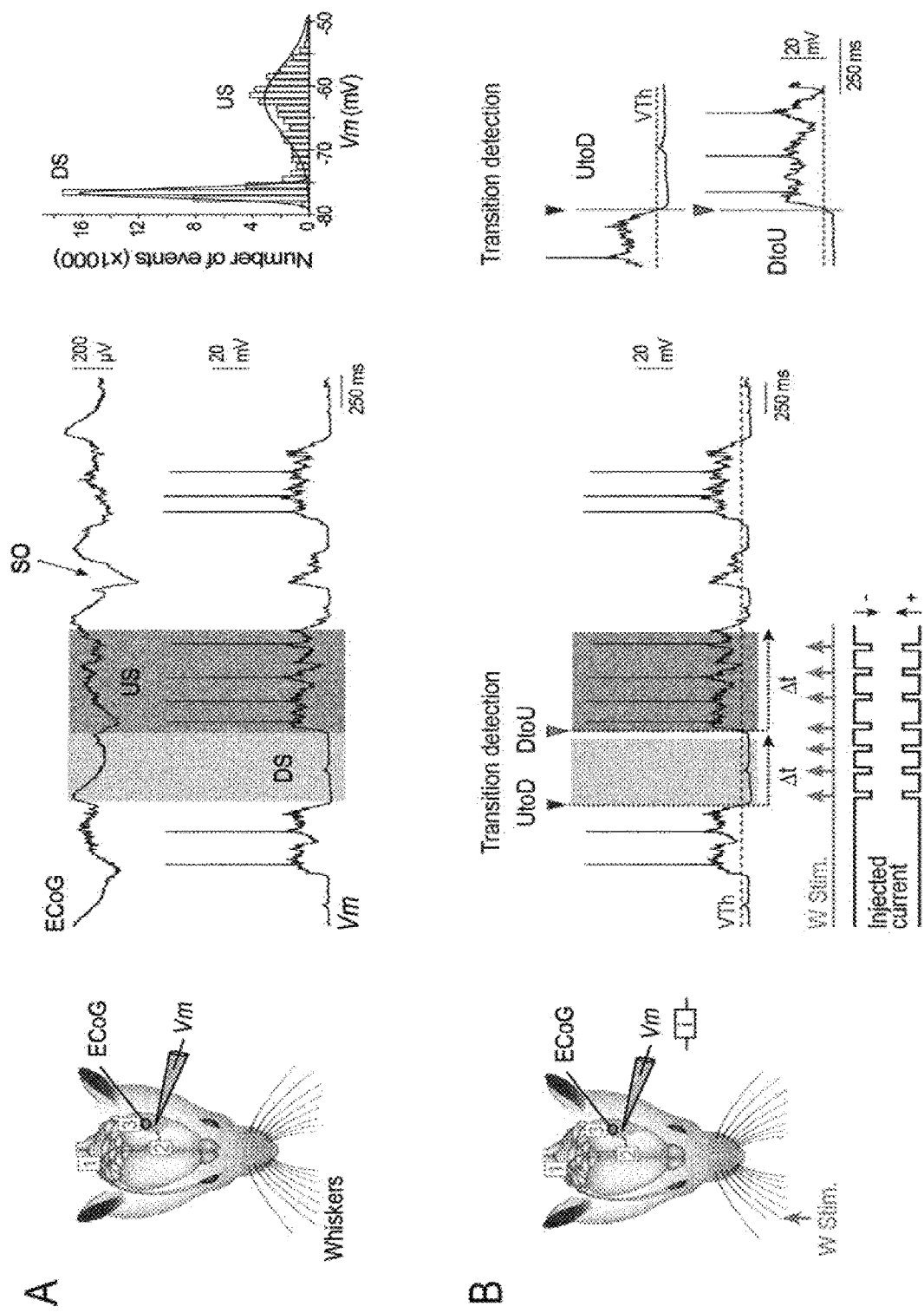
FIG. 5 represents diagrams showing recordings and stimulation procedures in the animal model.

Acute experiments in animals are conducted in parallel with human studies. These pre-clinical investigations, by allowing multi-scale (from neuronal population to single neurons) electrophysiological records, offer the possibility to determine the cellular and network mechanisms underlying sensory-evoked SO in humans. Simultaneous in vivo electrocorticographic (ECoG) and intracellular recordings of barrel cortex pyramidal neurons are performed in the anaesthetized rat (Mahon S, et al. (2012) J Neurosci. 32:11377-89; FIG. 1A, left). The barrel cortex is a specific region of the primary sensory cortex which receives and integrates sensory information from the whiskers. Rodents use these highly specialized sensory organs on their snout to constantly acquire sensory information from their environment (Petersen C C et al. Neuron. 2007 Oct. 25; 56(2):339-55). Rats are sedated by a systemic injection of a mixture of ketamine and xylazine, a pharmacological procedure generating a brain activity, including ECoG and intracellular patterns, highly similar to that encountered during SWS in humans and rodents (Destexhe A, et al. 2007 Trends Neurosci. 30: 334-42). In this model, ECoG activity is characterized by the recurrence of SO at ~1 Hz reflecting the alternance, at single cortical cell level, of prolonged depolarizations associated with action potential firing (up state, US) and periods of neuronal silence (down state, DS) (FIG. 5-A, right). Whisker stimuli (W Stim.) consisted in short puffs of air at low pressure (50 ms, 4-20 psi) delivered to whiskers contralateral to the site of neuronal recordings. Whisker stimuli were given at specific phases of the up and down states cycle using a close-loop feedback stimulation system (FIG. 5-B). Intracellular activity of single sensory cortical neurons is monitored and an adaptive voltage threshold (VTh) is used to detect transitions between up and down states. When the membrane potential (Vm) fell below Vth, an up to down state transition (UtoD) is detected. Conversely, when Vm rose above VTh, a down to up state transition (DtoU) is detected (FIG. 5-B). A transistor-transistor logic (TTL) pulse commands the sensory stimulation system with a given delay ($\Delta t$) after the detection of the transitions. Varying the time delays after transitions detection permits to explore and determine the best stimulation parameters (delay and intensity) for an optimal enhancement of SO. In some experiments, instead of sensory stimuli, we apply negative and positive direct current pulses through the intracellular electrode to test for changes in the excitability (i.e., the ability to fire an action potential) of cortical neurons during the up and down state cycle (FIG. 5-B). This will allow us to correlate possible changes in cortical excitability with the effectiveness of sensory stimuli in triggering SO.

Figure 6:
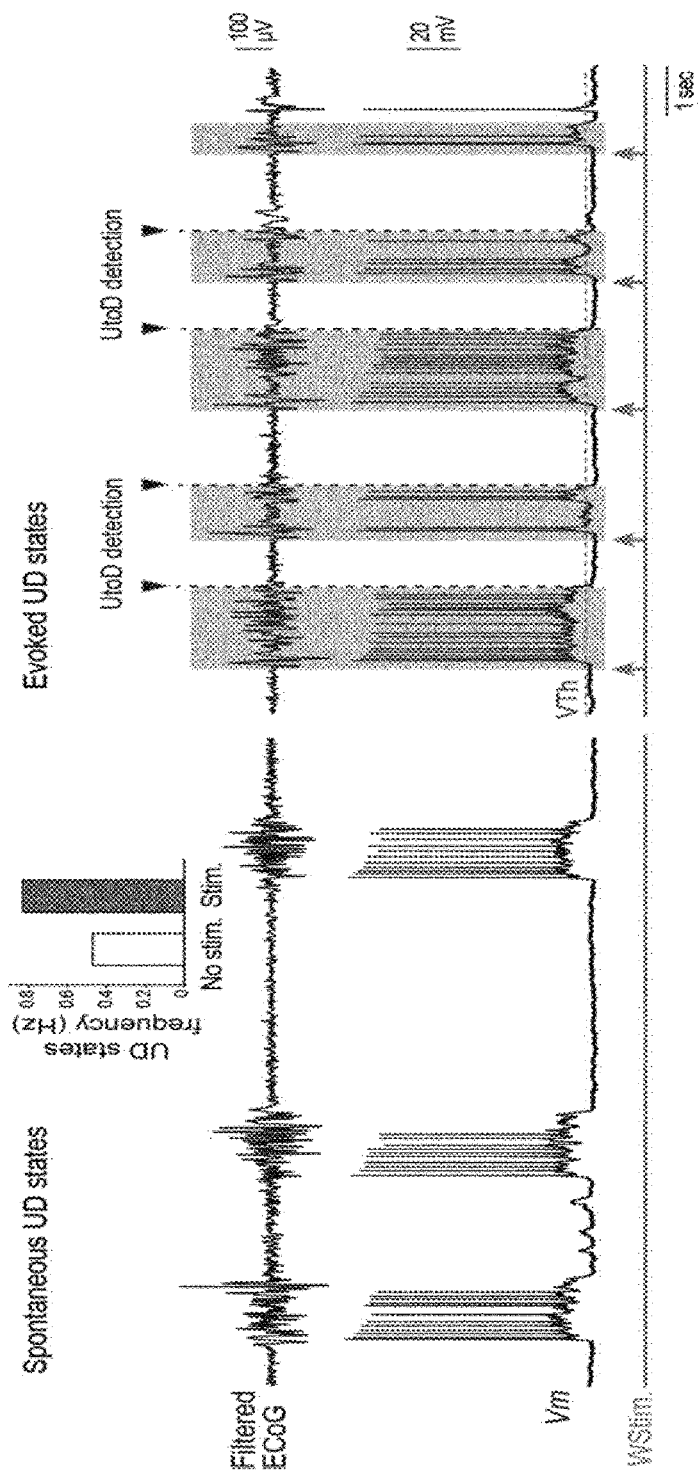
FIG. 6 represents diagrams showing sensory stimulations applied during the down state increase the number of up and down states and SO.
Figure 7:
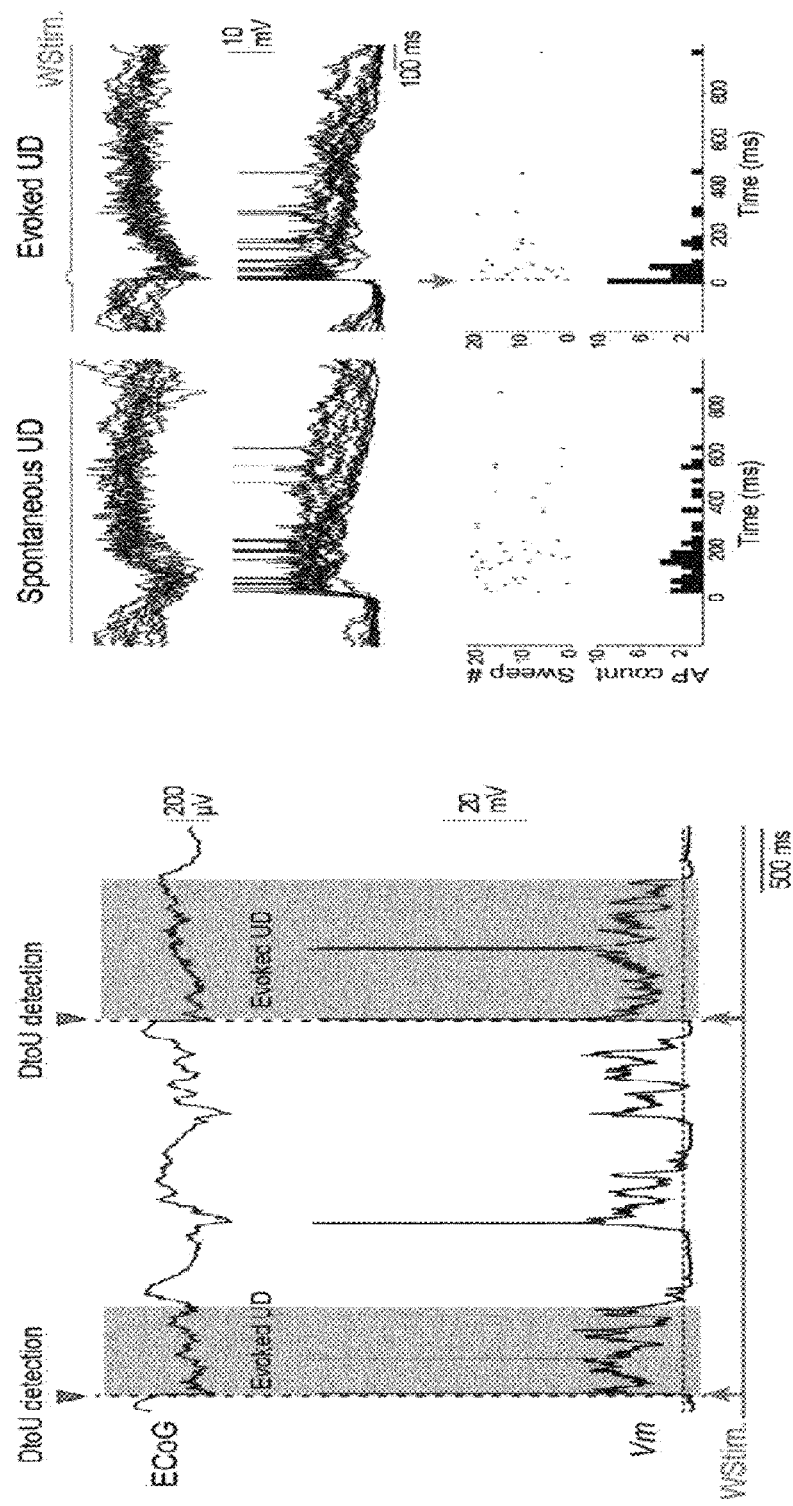
FIG. 7 represents diagrams showing sensory stimulations in phase with the ongoing up and down state oscillations modulate the pattern of action potential discharge in sensory cortical neurons.

Sensory stimuli given more than 150 ms after a transition to the down state are effective in inducing and increasing up down states oscillations in barrel cortex neurons. This effect is also visible at the level of the cortical neurons population expressed as sensory-evoked SO in the EcoG (FIG. 6). Sensory stimulation in phase with the spontaneous ongoing up and down state oscillations (i.e, sensory stimuli at 1 ms after the detection of a DtoU transition) are able to modify the pattern of action potential firing in the up state phase (FIG. 7). This change in firing pattern could be essential for the induction of cortical plasticity (Chauvette S et al. J Neurosci. 2011 Oct. 19; 31(42):14998-5008).

This is a crucial point since long-term synaptic plasticity is considered as a plausible cellular mechanism underlying sleep-dependent memory formation (Chauvette S et al. 2012 Neuron. 75:1105-13). In future experiments, to determine if sensory stimulations can trigger long-term plasticity at cortical synapses, the amplitude of synaptic responses evoked by local electrical stimulation, or by sensory stimuli, will be compared before and after the application of boosting stimuli. We will also search for long-term modifications in the intrinsic excitability of cortical neurons (Mahon S, et al. 2012 J Neurosci. 32:11377-89) that could also participate to memory formation (Daoudal G, et al. 2003 Learn Mem. 10:456-65).

CONCLUSION

It is thus expected that our new system can work as an artificial enhancer to boost natural sleep brain waves, including SO but also other sleep oscillations like thalamo-cortical spindles and hippocampal ripples. Because all these sleep oscillations are associated with memory processing, it is anticipated that the system can be applied in clinical settings to restore normal memory performance. Indeed, a number of disorders and diseases are accompanied by changes in sleep patterns and dysfunctions of memory, such as depression (Daoudal G, et al. 2003 Learn Mem. 10:456-65), post-traumatic stress disorder (Steiger A et al. 2013 Pharmacopsychiatry 46 (Suppl.1), S30-S35), Alzheimer's disease (Germain A 2013 Am. J. Psychiatry 170, 372-382) and schizophrenia (Wang G et al. 2011 Trends Neurosci. 34, 452-463). Also, SWS gradually reduces as people age, and may even be entirely absent after 65 or 70. The decline of memory is correlated with a reduction of SWS (Lu W and Goder R 2012 Sleep Med. Rev. 16, 389-394). In normal aging, closed loop stimulation for sleep enhancement can help the maintenance of healthy cognitive function and memory consolidation.

Example 3

Optimized Stimulation Protocols for Enhancing SOs

The time between the minimum SO deflection and its subsequent maximum is highly variable. Therefore, following a fixed double stimulation protocol (FIG. 8A), it can be observed that, while satisfactory results are obtained for the first stimulation (A, right: stimulation phase histogram alongside the corresponding SO shape), the second stimulation is often not at the maximum of the SO. Therefore we developed an adapted double stimulation protocol in which the stimulation timing is fitted to the SO period (K) and subsequent minimum points. The detection steps of the adaptative protocol (FIG. 8B) are:
 1) Detection of the negative pic (lower than the threshold) of the SO;
 2) Estimation of period K of the current wave (by zero crossing) and stimulation at adapted time K/2;
 3) Detection of the second negative pic and stimulation.

Figure 8:
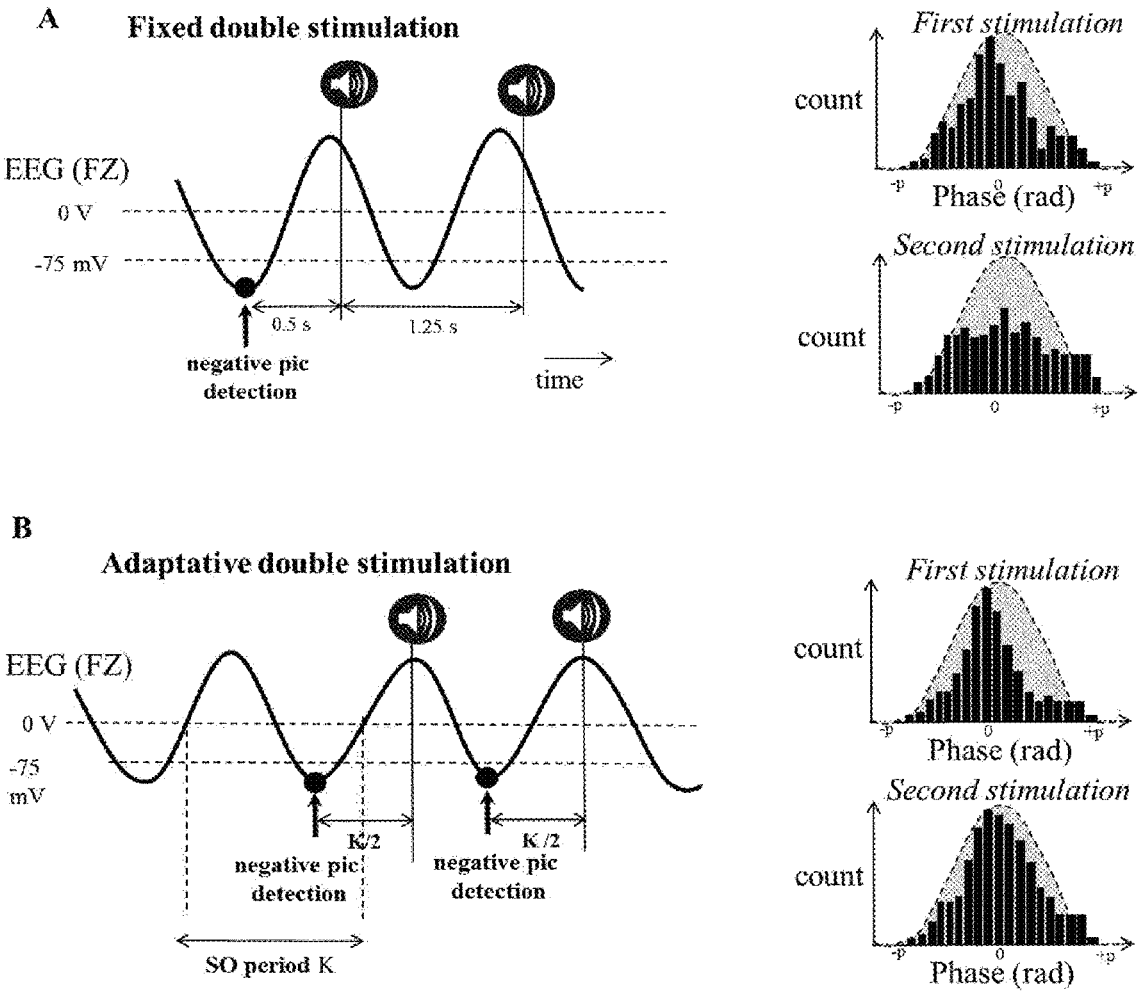
FIG. 8 represents recordings of SO shapes alongside with a stimulation phase histogram of a fixed double stimulation protocol (A) and an adaptative double stimulation protocol (B).

This protocol gives a better precision for the second stimulation mostly triggered during the maximum of the SO (FIG. 8B, right: stimulation phase histogram alongside the corresponding SO shape).

Figure 9:
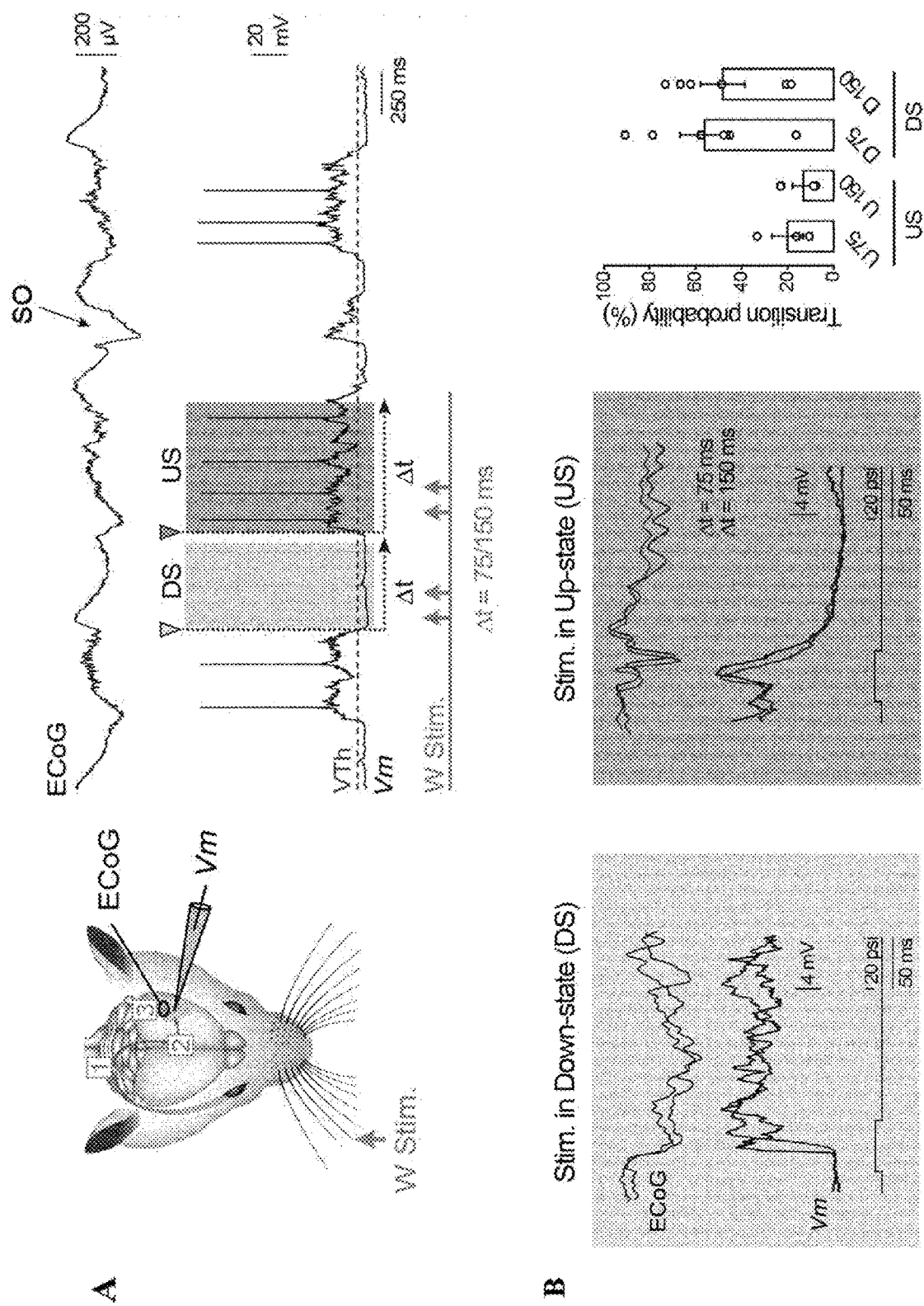
FIG. 9 represents diagrams showing recordings, SO detection and stimulation procedures in the animal model (A), and simultaneous electrocorticographic (ECoG) and intracellular (Vm) recordings from somatosensory pyramidal neurons illustrating the probability of evoking an SO as a function of the stimulation phase (B).

Simultaneous electrocorticographic (ECoG) and intracellular recordings from somatosensory pyramidal neurons are performed in rats under ketamine-xylazine (FIG. 9A-B). Slow oscillations (SO) in the ECoG are reflected by an alternation of depolarizing up-states (US) and hyperpolarizing down-states (DS) in cortical neurons. An adaptive voltage threshold (VTh) is used to detect transitions between US and DS. A high-voltage pulse commands the sensory stimulation system (W stim.) with a given delay (Δt) after the detection of the transitions. Varying the time delays after transitions detection permits to explore and determine the best stimulation parameters for an optimal enhancement of SO. Sensory stimuli delivered during the DS (75 or 150 ms after a transition to the DS) are more effective in triggering new oscillations in cortical neurons and networks compared to sensory stimuli delivered during the US.

The invention claimed is:

1. A non-invasive method for monitoring a subject's brain activity and emitting stimuli according to said subject's brain activity, said method comprising:
   I. receiving a brain activity signal measured by a monitoring device for measuring said subject's brain activity;
   II. monitoring said brain activity signal,
   III. detecting in said brain activity signal an end of a stage I of a non-REM light sleep state, by detection of a negative peak with an amplitude inferior to −75 μV, and an onset of a stage II of said non-REM light sleep state,
   IV. emitting a first stimulus at the detection of the onset of stage II of said non-REM light sleep state based on the brain activity signal,
   V. emitting a second stimulus,
   VI. repeating emitting the first stimulus and the second stimulus until an end of a stage IV of said non-REM light sleep state is detected basded on the the brain activity signal, and
   VII. restarting steps IV to VII when an onset of a further stage II of said non-REM light sleep state is detected based on the brain activity signal.

2. The non-invasive method according to claim 1, wherein said first or second stimulus is a sensory, electrical and/or magnetic stimulus.

3. The non-invasive method according to claim 1, wherein both stimulus and the second stimulus are separated for a time comprised from 0.5 second to 2.5 seconds.

4. The non-invasive method according to claim 1, wherein the first stimulus is emitted from 0.1 to 1 second after the detection of the negative peak in said brain activity signal.

5. The non-invasive method according to claim 1, further comprising:
   performing a memory training or a learning process, wherein the subject is awake during the memory training or the learning process; and
   emitting the first stimulus and the second stimulus during the memory training or the learning process.

6. The non-invasive method according to claim 1, wherein said method is controlled by said subject.

7. The non-invasive method according to claim 1, wherein said method is controlled by a skilled physician.

8. The non-invasive method according to claim 1, wherein said subject is a healthy subject which undergoes normal aging or a training period.

9. The non-invasive method according to claim 1, wherein said subject is affected by a memory-related disorder or a cognitive-related disorder.

10. The non-invasive method according to claim 1, wherein said subject is affected by a neuronal connectivity disorder.

11. A device for implementing a non-invasive method for monitoring a subject's brain activity and emitting stimuli according to said subject's brain activity, comprising:
   a. a monitoring device for measuring said subject's brain activity;
   b. a stimulation device providing a first stimulus and a second stimulus; and
   c. a programmable microcontroller board configured to perform the steps of:
      I. receiving a brain activity signal measured by said monitoring device;
      II. monitoring said brain activity signal;
      III. detecting in said brain activity signal the end of a stage I of a non-REM light sleep state by detection of a negative peak with an amplitude inferior to −75 μV and an onset of stage II of the non-REM light sleep state;
      IV. causing the stimulation device to emit the first stimulus at the detection of the onset of stage II of the non-REM light sleep state based on the brain activity signal;
      V. causing the stimulation device to emit the second stimulus;
      VI. causing the stimulation device to repeat the emission of the first stimulus and the second stimulus until an end of stage IV of the non-REM light sleep state is detected based on the brain activity signal; and
      VII. repeating steps IV to VII when the onset of stage II of the non-REM light sleep state is detected based on the brain activity signal.

12. The device according to claim 11, wherein the first stimulus or the second stimulus is a sensory, electrical and/or magnetic stimulus.

13. The device according to claim 11, wherein the first stimulus and the second stimulus are separated by a time interval comprised between 0.5 second to 2.5 seconds.

14. The device according to claim 11, wherein the first stimulus is applied from 0.1 to 1 second after the detection of the negative peak in said brain activity signal.

15. The device according to claim 11, further comprising a communication module.

16. The device according to claim 11, wherein said device is configured to be controlled by the subject.

17. The device according to claim 11, wherein said device is configured to be controlled by a skilled physician.

18. The device according to claim 11, wherein the programmable microcontroller board is further configured to perform a step of filtering said brain activity signal.

19. The device according to claim 11, further comprising a computer-readable storage medium.

20. The device according to claim 11, further comprising a user interface.

21. The device according to claim 20, wherein the user interface is configured to visualize physiological parameters of the subject.

* * * * *